United States Patent [19]

Dubroeucq et al.

[11] 4,402,961
[45] Sep. 6, 1983

[54] DERIVATIVES OF 1-(2-,3- OR 4-QUINOLYL)-2- OR -3-(2- OR 3-PIPERIDYL OR -PYRROLIDINYL) ETHANONE OR PROPANONE, AND THEIR UTILIZATION AS ANTIARRHYTHMICS, ANTICONVULSIVANTS AND FOR THE TREATMENT OF ANXIETY

[75] Inventors: Marie-Christine Dubroeucq, Enghien-les-Bains; Claude G. A. Gueremy, Houilles; Gérard R. Le Fur, Plessis Robinson; Jacques Mizoule, Villeneuve la Garenne, all of France

[73] Assignee: Pharmindustrie, Gennevilliers, France

[21] Appl. No.: 271,877

[22] Filed: Jun. 9, 1981

[30] Foreign Application Priority Data

Jun. 20, 1980 [FR] France ............................ 80 13698

[51] Int. Cl.³ ................... A61K 31/47; C07D 401/06
[52] U.S. Cl. ................................. 424/258; 546/167; 546/168; 546/173; 546/176
[58] Field of Search ............... 546/167, 168, 173, 176; 424/258

[56] References Cited

U.S. PATENT DOCUMENTS

| | | | |
|---|---|---|---|
| 2,492,487 | 12/1949 | Koepfli et al. | 546/176 X |
| 3,857,837 | 12/1974 | Gutzwiller et al. | 546/176 X |
| 3,953,453 | 4/1976 | Grethe et al. | 546/134 |
| 4,237,139 | 12/1980 | Champseix et al. | 424/258 |
| 4,238,612 | 12/1980 | Barieux et al. | 546/153 |
| 4,299,835 | 11/1981 | Champseix et al. | 424/258 |

FOREIGN PATENT DOCUMENTS 2206944 6/1974 France ............................ 546/176

OTHER PUBLICATIONS

Heidelberger et al., J. Am. Chem. Soc., vol. 44, pp. 1098–1107 (1922).
Wirth Chemical Abstracts, vol. 76, 103,776f (1972).
Wirth, Chemical Abstracts, vol. 80, 124,762w (1974).
Gutzwiller et al., J. Am. Chem. Soc., vol. 100, No. 2, pp. 576–581, 1978.
Grethe, Chemical Abstracts, vol. 83, 114,718j (1975).
Wagner et al., "Synthetic Organic Chemistry", p. 5, J. Wiley & Sons (1953).
"Organic Reactions", vol. 5, p. 301, John Wiley & Sons (1949).

Primary Examiner—Donald G. Daus
Assistant Examiner—Diana G. Rivers

Attorney, Agent, or Firm—Beveridge, DeGrandi and Kline

[57] ABSTRACT

Compounds, useful as medicaments, of the formula:

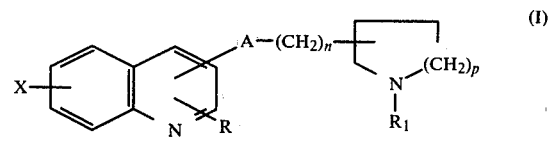

(I)

in which R is fixed in position 2 or 4 on the cycle of the quinoline and indicates a hydrogen atom or an alkyl group containing 1 to 4 carbon atoms, pyridyl, thienyl, phenyl or substituted phenyl group, X is fixed in position 5, 6, 7 or 8 on the cycle of the quinoline and indicates a hydrogen or halogen atom or an alkyl, alkoxy or alkylthio group containing 1 to 4 carbon atoms or $CF_3$ group, $R_1$ is a hydrogen atom or an alkyl containing 1 to 4 carbon atoms, alkenyl containing 3 to 4 carbon atoms or arylalkyl group, A is a CO, CHOH, or $CH_2$ group, n and p are equal to 1 or 2, the group

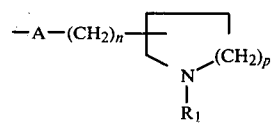

is fixed in position 2, 3 or 4 on the cycle of the quinoline and the group

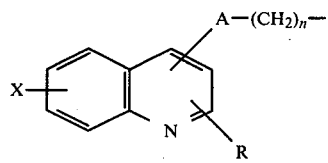

is fixed in position 2 or 3 on the nitrogen heterocycle

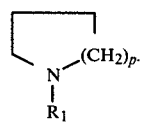

16 Claims, No Drawings

DERIVATIVES OF 1-(2-,3- OR 4-QUINOLYL)-2- OR -3-(2- OR 3-PIPERIDYL OR -PYRROLIDINYL) ETHANONE OR PROPANONE, AND THEIR UTILIZATION AS ANTIARRHYTHMICS, ANTICONVULSIVANTS AND FOR THE TREATMENT OF ANXIETY

The present invention relates to new derivatives of 1-(2-, 3- or 4-quinolyl)-2- or -3-(2- or 3-piperidyl or -pyrrolidinyl)ethanone or propanone which can be used as medicaments or as intermediate products for the preparation of medicaments.

These derivatives may be represented by the general formula:

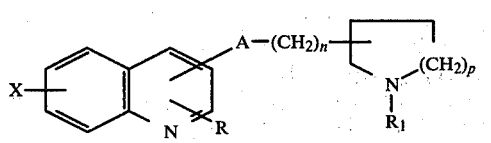

(I)

in which R is fixed in position 2 or 4 on the cycle of the quinoline and represents a hydrogen atom, an alkyl group having 1 to 4 carbon atoms, a phenyl, pyridyl or thienyl group, or a phenyl group substituted by one or two substituents selected from the halogen atoms (chlorine, fluorine, bromine), alkyl, alkoxy and alkylthio groups having 1 to 4 carbon atoms and the trifluoromethyl group.

X is fixed in position 5, 6, 7 or 8 on the quinoline cycle and represents a hydrogen or halogen (chlorine, fluorine, bromine) atom, an alkyl, alkoxy or alkylthio group having 1 to 4 carbon atoms or a trifluoromethyl group.

$R_1$ represents a hydrogen atom, an alkyl group containing 1 to 4 carbon atoms, an alkenyl group containing 3 or 4 carbon atoms or an arylalkyl, especially phenylalkyl group, of which the alkyl part contains 1 to 3 carbon atoms, A represents a CO, CHOH or $CH_2$ group, n is a whole number equal to 1 or 2, p is a whole number equal to 1 or 2, the group:

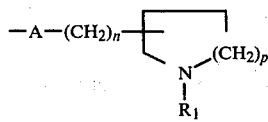

is fixed in position 4 or 2 on the quinoline cycle, and can also be fixed in position 3 on the same cycle when R is a hydrogen atom, and the group:

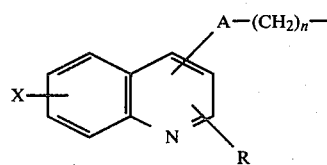

is fixed in position 2 or 3 on the nitrogen heterocycle:

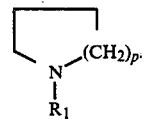

As indicated in formula (I) above, the compounds according to the invention contain a pyrrolidine cycle (when p=1) or a piperidine cycle (when p=2).

When A is a CO or $CH_2$ group, the molecule of the compounds of formula (I) contains an asymmetric carbon atom and then, for a given significance of R, X, A, $R_1$, n and p, there is a racemic form and two enantiomers corresponding to the planar formula (I). When A is a CHOH group, the molecule of the compound of formula (I) contains two asymmetric carbon atoms and then, for a given significance of R, X, $R_1$, n and p, there are two diastereoisomers corresponding to the planar formula (I). A racemic form and two enantiomers correspond to each diastereoisomer.

In formula (I) of the compounds according to the invention, X is preferably a hydrogen atom, R a phenyl group and n is preferably equal to 1.

The compounds of formula (I) for which A represents the $CH_2$ group may be prepared by reduction of the corresponding compounds of formula (I) for which A represents the CO group.

Methods, known per se, which enable a CO group to be converted into a $CH_2$ group, are used for this reduction, for example those described by R. B. Wagner and H. D. Zook (Synthetic Organic Chemistry, p. 5, J. Wiley and Sons—1953). The reducing agent used is advantageously hydrazine hydrate in the presence of an alkali metal hydroxide such as sodium or potassium hydroxide, in an inert solvent such as an alcohol or a diol, for example diethyleneglycol or ethyleneglycol, at a temperature between 100° and 180° C.

The compounds of formula (I) for which A represents the CHOH group may be prepared by reduction of the corresponding compounds of formula (I) for which A represents the CO group by means of a reducing hydride. The reducing hydride used may be, for example, sodium or potassium borohydride, in an alcohol such as methanol or ethanol, possibly in the presence of water. There may also be used aluminum lithium hydride in an inert solvent such as diethyl ether, tetrahydrofuran or a hydrocarbon. These hydrides are generally used in excess, at a temperature between 0° C. and the boiling temperature of the solvent used.

The compounds of formula (I) for which A represents the CO group and $R_1$ a hydrogen atom may be prepared by condensation of an ester of quinolinecarboxylic acid of formula (II) with an ester of formula (III), then hydrolysis and decarboxylation of the compound of formula (IV) thus obtained, according to the following reaction diagram:

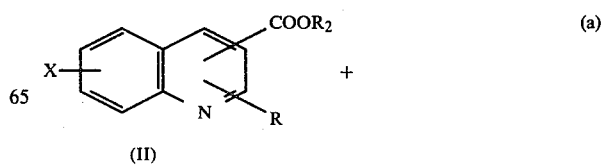

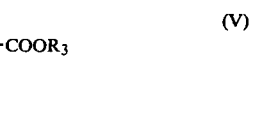

(III)

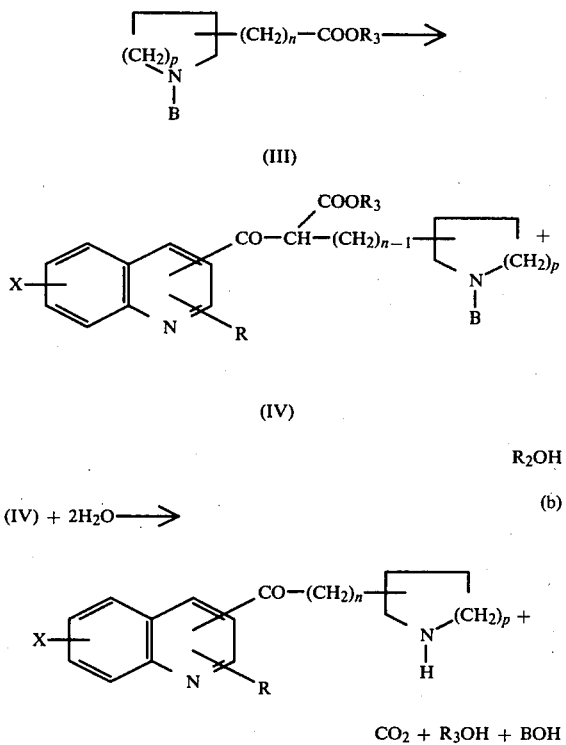

In the formulae (II), (III) and (IV) above, X, R, n and p have the same significance as in formula (I), $R_2$ and $R_3$ represent alkyl groups of low molecular weight, for example methyl or ethyl, and B represents a group protecting the amine function, which is stable in anhydrous alkaline medium and can be removed in acid medium, such as those which are described by R. A. Boissonnas, Advances in Organic Chemistry 3, p. 159, Interscience (1963). As group B an acyl group is advantageously used, such as the benzoyl group, the benzyloxycarbonyl group or the triphenylmethyl group.

In order to carry out the condensation reaction (a), processes known per se are used (cf. "The Acetoacetic Acid Ester Condensation", C. R. Hauser et al., Organic Reactions, vol. 1, p. 266, Wiley and Sons, 1942). Advantageously the operation is effected in the presence of a base such as an alcoholate (for example potassium tertiobutylate) or a metal hydride (for example sodium or potassium hydride), in an inert solvent such as a hydrocarbon or another aprotic solvent (for example tetrahydrofuran), at a temperature between 0° C. and the boiling temperature of the solvent used.

The hydrolysis reaction (b) is carried out according to processes known per se (cf. "Cleavage of β-keto-esters", R. B. Wagner and H. D. Zook, Synthetic Organic Chemistry, p. 327, Wiley and Sons, 1953). The most usual method consists in heating at the boil the product of formula (IV) in an aqueous solution of an acid such as hydrochloric or sulfuric acid.

The starting products of formula (II) are easily accessible by methods described in the literature (cf. Quinolines-Heterocyclic Compounds—32, 274, Wiley and Sons, 1977). The products of formula (III) can be prepared, for example, by benzoylation of esters of the formula:

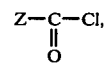

(V)

In the benzoylation reaction, benzoyl chloride is advantageously used, generally in the presence of a base such as triethylamine or an alkali metal carbonate, in an inert solvent such as chloroform, at a temperature between 0° C. and 50° C.

The esters of formula (V) for which $R_3$ is the ethyl group are known products. The other esters of formula (V) can be prepared by known processes described in the literature.

The compounds of general formula (I) for which $R_1$ is an alkyl, alkenyl or arylalkyl group may be prepared by the action of an alkylating agent on the corresponding compounds of formula (I) for which $R_1$ is a hydrogen atom. Suitable alkylating agents are halides of the formula $R_1$Hal, sulfates of the formula $(R_1)_2SO_4$ and alkyl- or aryl-sulfonates of the formula Ar $SO_3R_1$ or $R'SO_3R_1$, in which formulae $R_1$ represents an alkyl group having 1 to 4 carbon atoms, an alkenyl group having 3 or 4 carbon atoms or an arylalkyl group of which the alkyl part has 1 to 3 carbon atoms, Ar represents an aryl group and R' represents an alkyl group.

The alkylation reaction of the compounds of formula (I) for which $R_1 = H$ by means of an alkylating agent is carried out according to processes known per se. Advantageously the operation is effected in the presence of an organic or mineral base (for example sodium or potassium carbonate) in an inert solvent, for example dimethylformamide.

The compounds of formula (I) for which $R_1$ represents the methyl group and A the $CH_2$ group can also be prepared by the action of formaldehyde in formic acid on the corresponding compounds of formula (I) for which $R_1$ is a hydrogen atom (Leuckart reaction—cf. Organic Reactions, Vol. 5, p. 301, John Wiley and Sons, 1949). This reaction is advantageously effected at a temperature near to 100° C.

A variant for the preparation of the products of general formula (I) for which A represents the $CH_2$ group and $R_1$ an alkyl group containing 2 to 4 carbon atoms or an arylalkyl group, comprises reacting the corresponding products of formula (I) for which A represents the $CH_2$ group and $R_1$ a hydrogen atom with an acid chloride of the formula $$Z-\underset{\underset{O}{\|}}{C}-Cl,$$

in which Z represents an alkyl group having 1 to 3 carbon atoms, an aryl group or an arylalkyl group the alkyl part of which has one or two carbon atoms, and then reducing by means of a hydride the compound of formula (VI) thus obtained, according to the following reaction scheme:

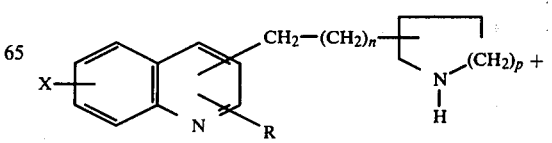

-continued

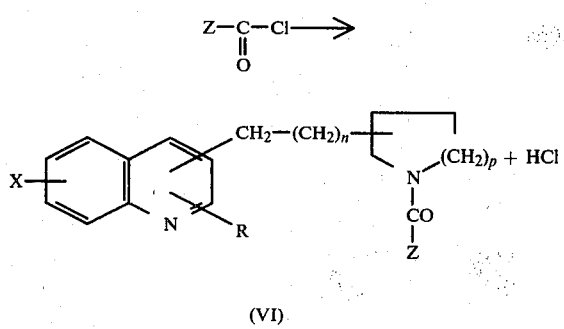

(VI)

(VI) $\xrightarrow{\text{reducing}}_{\text{hydride}}$ (d)

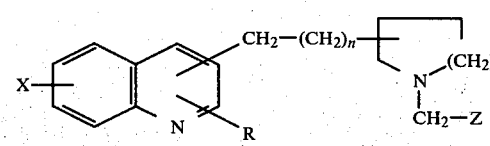

In order to carry out reaction (c) methods known per se are used, which enable a secondary amine to be converted into an amide, for example those described by R. B. Wagner and H. D. Zook (Symthetic Organic Chemistry, p. 565 and p. 646, J. Wiley and Sons, 1953). The operation is generally effected in the presence of a base such as triethylamine, in an inert solvent such as chloroform at a temperature between 0° C. and 50° C.

Reaction (d) also uses methods known per se. Advantageously the reducing hydride used is aluminum lithium hydride, in an inert solvent such as an ether (for example diethyl oxide, tetrahydrofuran) or an aromatic hydrocarbon, at a temperature between 0° C. and the boiling temperature of the solvent used.

The products of formula (I) corresponding to the formula:

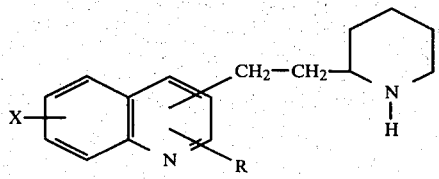

(VII)

may also be prepared by catalytic hydrogenation of the pyridine derivatives of the formula:

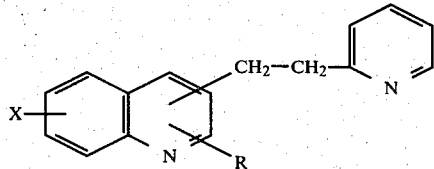

(VIII)

In order to carry out this hydrogenation, the operation is advantageously effected at a temperature between 20° C. and 60° C. under a pressure of hydrogen near to 1 bar, in the presence of platinum oxide as catalyst and in an inert solvent such as acetic acid or a mixture of an alcohol (especially methanol or ethanol) and an acid (especially acetic acid or hydrochloric acid).

The compounds of formula (VIII) may be prepared by the reaction of 2-methyl-pyridine with a metal derivative of formula R"M, in which M indicates an alkali metal (especially lithium, sodium, potassium) and R" indicates a hydrogen atom, an NH$_2$ group, a disubstituted amino group or an alkyl or aryl group, reaction of the metallated 2-methyl-pyridine of formula (IX) thus obtained with an ester of quinolinecarboxylic acid of formula (II) and reduction of the carbonyl derivative of formula (X) thus obtained. All these reactions can be shown diagrammatically as follows:

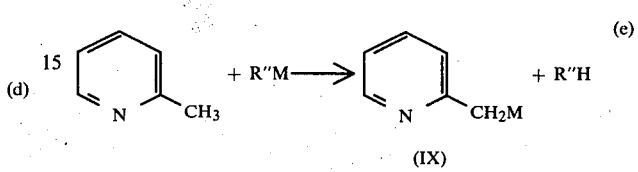

(e)

(IX)

(IX) + (II) ⟶  (f)

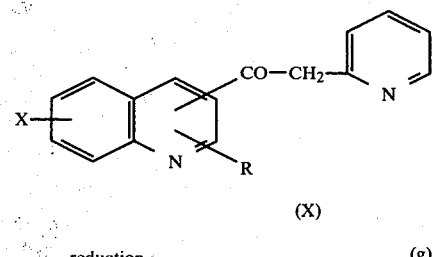

(X)

(X) $\xrightarrow{\text{reduction}}$ (VIII)     (g)

Reactions (e) and (f) are effected in an inert solvent such as an ether (for example diethyl oxide, tetrahydrofuran or dimethoxyethane), preferably at a temperature between −60° C. and −70° C. As metal derivative R"M there is preferably used a lithium derivative, for example phenyllithium, butyllithium or lithium diisopropylamide.

For reaction (g) the reducing agent advantageously used is hydrazine hydrate in the presence of an alkali metal hydroxide such as sodium or potassium hydroxide, in an inert solvent such as an alcohol or a diol, for example diethyleneglycol, at a temperature between 100° C. and 180° C.

The compounds of formula (I) corresponding to the formula:

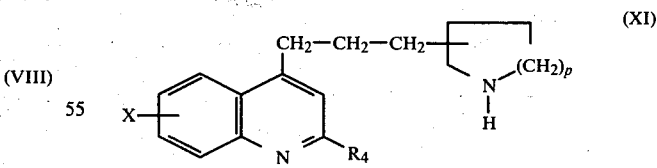

(XI)

in which X and p have the same significance as in formula (I) and R$_4$ indicates a hydrogen atom, a phenyl group or a phenyl group substituted by one or two substituents selected from the halogen atoms, the alkyl, alkoxy and alkylthio groups having 1 to 4 carbon atoms and CF$_3$, can also be prepared by the reaction of a metal derivative R"M such as previously defined with a quinoline derivative of formula (XII), reaction of the compound of formula (XIII) thus obtained with a compound of the formula:

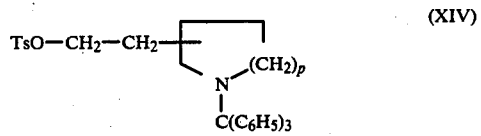

in which Ts indicates the tosyl group, that is the group

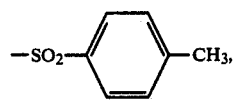

and the action of an acid on the compound of formula (XV) thus obtained. All these reactions can be shown diagrammatically as follows:

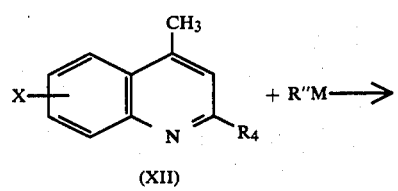

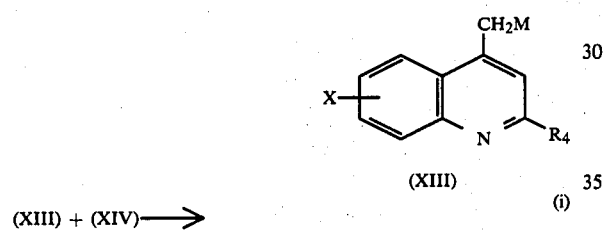

(XIII) + (XIV) ⟶

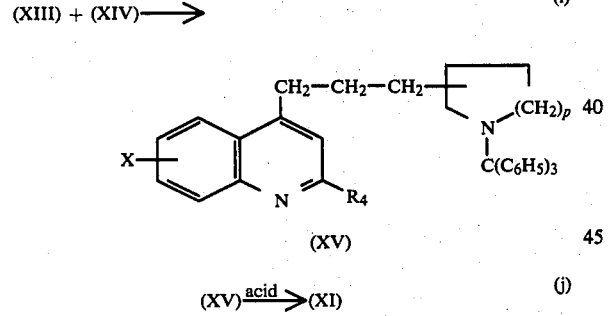

(XV) $\xrightarrow{\text{acid}}$ (XI)   (j)

Reactions (h) and (i) are effected in an inert solvent such as an ether (for example diethyl oxide, tetrahydrofuran or dimethoxyethane), at a temperature which is a function of the metal derivative R″M used and which can range from −70° C. to the boiling temperature of the solvent used. As the metal derivative R″M there is preferably used a lithium derivative, for example phenyllithium, butyllithium or lithium diisopropylamide, in which case reaction (h) is effected at a temperature of −70° C. to 0° C. and reaction (i) at a temperature between −70° C. and the ambient temperature.

Reaction (j), which consists in replacing the protecting triphenylmethyl group by a hydrogen atom, is effected by treating the compound of formula (XV) by an acid such as hydrochloric acid, in a water-alcohol medium, at a temperature between 20° C. and 70° C.

The compounds of formula (XIV) may be prepared by the reaction of triphenylmethyl chloride on an ester of the formula:

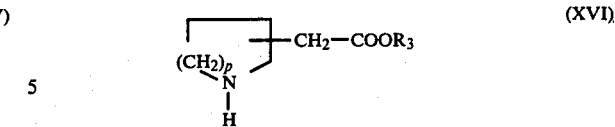

in which $R_3$ indicates an alkyl group of low molecular weight, for example methyl or ethyl, reduction by lithium aluminum hydride $LiAlH_4$ of the ester of formula (XVII) thus obtain and action of tosyl chloride on the alcohol of formula (XVIII) obtained. All these reactions may be shown diagrammatically as follows:

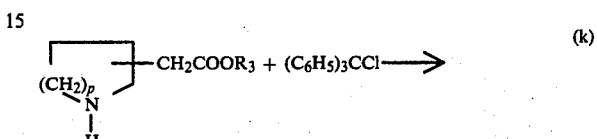

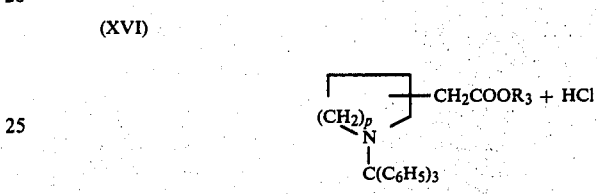

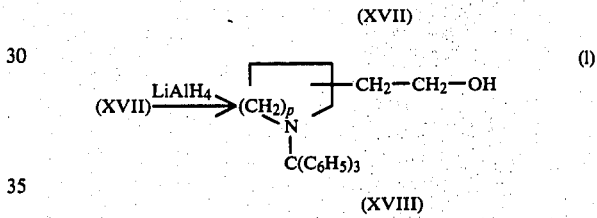

(XVIII) + CH$_3$—⟨⟩—SO$_2$—Cl ⟶ (XIV)   (m)

Reaction (k) is advantageously effected in an inert solvent which permits the solubilization of the reagents, for example chloroform, and in the presence of a base such as a tertiary amine (for example triethylamine). Reaction (l) is effected in an inert solvent, preferably an ether such as diethyl oxide or tetrahydrofuran, at a temperature between 0° C. and the ambient temperature. Reaction (m) is effected in an inert solvent and in the presence of a base, preferably an amine. An advantageous method consists in operating in pyridine, which plays the part both of solvent and base, at a temperature between 0° C. and 20° C.

The reaction mixtures obtained by the various processes previously described are treated by conventional methods, physical (evaporation, extraction with a solvent, distillation, crystallization, chromatography, etc.) or chemical (formation of salt and regeneration of the base, etc.) in order to isolate the compounds of formula (I) in the pure state.

The compounds of formula (I) in the form of the free base may possibly be converted into salts of addition with a mineral or organic acid by the action of such as acid in a suitable solvent.

The medicaments of the benzodiazepines class are used as anticonvulsivants, as hypnotics and for the treatment of states of anxiety and of various psychoneurotic states. The presence of specific receptors of benzodiazepines in the membranes of the rat brain has been demonstrated [Squires et Coll., Nature, 266, (1977), 732] and the degree of affinity of the benzodiazepines for these receptors, which is measured by their aptitude for displacing the tritiated Diazepan from its binding sites, is in good correlation with the pharmacodynamic effects observed on the animal and on man.

The products of the invention, although they have a structure different from those of the benzodiazepines, displace the Diazepam from its binding sites. They can therefore find applications as hypnotics, as anticonvulsivants, and in the treatment of the states of tension and anxiety resulting from "stress" circumstances or of somatic troubles bound up with emotional factors. They can be used for the treatment of the psychoneurotic states which are manifested by symptoms of anxiety, apprehension, fatigue, agitation or depression.

On the other hand, the products of the invention possess antiarrhythmic properties.

The following Examples illustrate the invention without it being limited thereto. The data relative to the spectra of nuclear magnetic resonance (in abridged form: N.M.R. spectra) which appear in these examples concern the nuclear magnetic resonance of the protons of the compounds in the form of the base. In order to effect the measurements of nuclear magnetic resonance the compounds are dissolved in deuteriated chloroform.

EXAMPLE 1

1-[4-(6-methoxy)quinolyl]-3-(3-piperidyl)-1-propanone 30 ml of a 20% suspension of potassium hydride in oil are added drop by drop to a solution of 14 g of ethyl(6-methoxyquinoline)-4-carboxylate in 200 ml of dry tetrahydrofuran, placed under a nitrogen atmosphere. There is then added slowly, in two hours, a solution of 14.5 g of ethyl 3-([3-(N-benzoyl)piperidyl]propionate in 100 ml of dry tetrahydrofuran, and the mixture is stirred at 25° C. for 3 hours. Then 20 ml of ethanol are added, the solvent is removed by distillation under reduced pressure, the residue is taken up with 300 ml of a 5 N aqueous solution of hydrochloric acid and heated under reflux for 22 hours. The aqueous solution is extracted 4 times, each by 100 ml of diethyl ether, then brought to pH 11 by addition of potassium hydroxide and extracted 3 times, each by 200 ml of ethyl acetate. The ethyl acetate phase is washed with water and dried over magnesium sulfate. After removal of the solvent under reduced pressure, 10 g of crude product are obtained. This product is absorbed on a column containing 300 g of silica. After elution with a 9/1 chloroform-diethylamine mixture, 9.1 g of 1-[4-(6-methoxy)quinolyl]-3-(3-piperidyl)-1-propanone are obtained, the monohydrochloride of which, formed in acetone by addition of a 5.8 N solution of hydrochloric acid in diethyl ether, melts at 169° C.

The ethyl 3-[3-(N-benzoyl)piperidyl]propionate may be prepared in the following way:

43 g of potassium carbonate are added to a stirred solution of 16.8 g of ethyl 3-(3-piperidyl)propionate (prepared as indicated in U.S. Pat. No. 3,159,639) in 150 ml of chloroform. The mixture is cooled to 10° C., then 16 g of benzoyl chloride are run in in 15 minutes. The mixture is then heated under reflux for 4 hours. The reaction medium is evaporated under reduced pressure. The residue is taken up with an aqueous solution of sodium bicarbonate and extracted with ethyl acetate. The organic phase is dried over magnesium sulfate and evaporated under reduced pressure. The residue is fixed on a column containing 500 g of silica and eluted with a 5/5 cyclohexane-ethyl acetate mixture.

15.7 g of ethyl 3-[3-(N-benzoyl)piperidyl]propionate in the form of an oil are thus isolated.

N.M.R spectrum of the product obtained:

The chemical shifts δ of the protons are the following:

| protons of the aromatic nucleus | $\delta = 7.4$ ppm |
| —$CH_2$—CO— | $\delta \simeq 2.2$ ppm |
| —$CH_2$—N— | $\begin{cases} \delta \simeq 4 \text{ ppm (equatorial)} \\ \delta \simeq 2.9 \text{ ppm (axial)} \end{cases}$ |

EXAMPLE 2

1-[4-(6-methoxy)quinolyl]-2-(3-piperidyl)-ethanone

The operation is as in Example 1, but starting from 4.2 g of ethyl(6-methoxy-quinoline)-4-carboxylate, 4.2 g of ethyl [3-(N-benzoyl)piperidyl]acetate and 12 ml of a 20% suspension of potassium hydride in oil. After fixation of the crude product on a column of silica and elution with the 9/1 chloroform-diethylamine eluant, 4 g of 1-[4-(6-methoxy)quinolyl]-2-(3-piperidyl)ethanone are obtained. This last compound is dissolved in acetone and converted by addition of hydrochloric acid into its monohydrochloride, which melts at 203° C.

The ethyl [3-(N-benzoyl)piperidyl]acetate can be prepared in the following way:

The operation is the same as for the preparation of the ethyl 3-[3-(N-benzoyl)piperidyl]propionate, but starting from 22.6 g of ethyl(3-piperidyl)acetate (which may be prepared as indicated by Woldemar et al., Arch. Pharm. 300 (6), 540-7 (1967), 23.5 g of benzoyl chloride and 63.2 g of potassium carbonate. 18 g of ethyl [3-(N-benzoyl)-piperidyl]acetate are thus obtained. N.M.R. Spectrum of the product obtained:

| protons of the aromatic nucleus | $\delta = 7.4$ ppm |
| —$CH_2$—CO— | $\delta \simeq 2.2$ ppm |
| —$CH_2$—N— | $\begin{cases} \delta \simeq 4 \text{ ppm (equatorial)} \\ \delta \simeq 3 \text{ ppm (axial)} \end{cases}$ |

EXAMPLE 3

1-[4-(2-phenyl)quinolyl]-2-(3-piperidyl)-ethanone 36 ml of a 20% suspension of potassium hydride in oil are slowly added to 200 ml of dry tetrahydrofuran, under an atmosphere of nitrogen. Then a solution of 18 g of ethyl(2-phenylquinoline)-4-carboxylate in 20 ml of dry tetrahydrofuran is introduced, and a solution of 16.5 g of ethyl [3-(N-benzoyl)piperidyl]acetate in 100 ml of dry tetrahydrofuran is slowly added over a period of two hours. The mixture is stirred for 5 hours at the ambient temperature. Then 20 ml of ethanol are added, the solvent is removed by distillation under pressure, the residue is taken up with 300 ml of a 5 N aqueous solution of hydrochloric acid and is heated under reflux for 13 hours. The aqueous phase is extracted 3 times, each by 300 ml of diethyl ether, then made alkaline by addition of concentrated ammonia and extracted 3 times, each by 200 ml of ethyl acetate. The ethyl acetate phase is washed with water and dried over magnesium sulfate. After elimination of the solvent by distillation under reduced pressure, 16.2 g of crude product are obtained which is absorbed on a column containing 810 g of silica. After elution with a 9/1 chloroform-diethylamine mixture, 12.4 g of 1-[4-(2-phenyl)quinolyl]-2-(3-piperidyl)-ethanone are obtained, which is converted into the monohydrochloride. This monohydrochloride melts at 218° C.

EXAMPLE 4

1-[4-(2-phenyl-quinolyl]-3-(3-piperidyl)-1-propanone

The operation is as in Example 1, but starting from 6 g of ethyl(2-phenyl-quinoline)-4-carboxylate, 5.8 g of ethyl 3-[3-(N-benzoyl)piperidyl]propionate and 12 ml of a 20% solution of potassium hydride in oil. 3.8 g of crude product are obtained, which are absorbed on a column containing 380 g of silica. After elution with a 93/7 chloroform-diethylamine mixture, 2.3 g of 1-[4-(2-phenyl)quinolyl]-3-(3-piperidyl)-1-propanone are obtained. The later compound is converted into its monohydrochloride. This monohydrochloride melts at 224° C.

EXAMPLE 5

1-(4-quinolyl)-3-(3-piperidyl)-1-propanone

On operating as in Example 1, but starting from 4.4 g of ethyl quinoline-4-carboxylate, 5.6 g of ethyl 3-[3-(N-benzoyl)piperidyl]propionate and 12 ml of a 20% suspension of potassium hydride in oil, 2.7 g of crude product are isolated, which are absorbed on a column containing 270 g of silica. After elution with a 9/1 chloroform-diethylamine mixture, 1.2 g of 1-(4-quinolyl)-3-(3-piperidyl)-1-propanone are obtained, which is converted into its monohydrochloride. This monohydrochloride melts at 163° C.

EXAMPLE 6

1-(2-quinolyl)-3-(3-piperidyl)-1-propanone

The operation is as in Example 1, starting from 14 g of ethyl quinoline-2-carboxylate, 17.4 g of ethyl 3-[3-(N-benzoyl)piperidyl]propionate and 36 ml of a 20% suspension of potassium hydride in oil. 7.4 g of 1-(2-quinolyl)-3-(3-piperidyl)-1-propanone are obtained, which is converted into its monohydrochloride. This monohydrochloride is recrystallized from ethanol. Its melting point, after recrystallization from ethanol, is 198° C.

EXAMPLE 7

1-(3-quinolyl)-3-(3-piperidyl)-1-propanone

The operation is as in Example 1, but starting from 4.5 g of ethyl quinoline-3-carboxylate, 6 g of ethyl 3-[3-(N-benzoyl)piperidyl]propionate and 13 ml of a 20% suspension of potassium hydride in oil. 3 g of crude 1-(3-quinolyl)-3-(3-piperidyl)-1-propanone are obtained.

EXAMPLE 8

1-[4-(6-chloro-2-phenyl)quinolyl]-2-(3-piperidyl)-ethanone

The operation is as in Example 3, but starting from 12.2 g of ethyl(6-chloro-2-phenyl-quinoline)-4-carboxylate, 8.25 g of ethyl [3-(N-benzoyl)piperidyl]acetate and 18 ml of a 20% suspension of potassium hydride in oil. 8.1 g of 1-[4-(6-chloro-2-phenyl)quinolyl]-2-(3-piperidyl)-ethanone are obtained. This last compound is dissolved in acetone and converted, by addition of hydrochloride acid, into its monohydrochloride, which melts at above 260° C.

EXAMPLE 9

1-{4-[2-(3-trifluoromethyl-phenyl)]quinolyl}-2-(3-piperidyl)-ethanone 30 ml of a 20% suspension of potassium hydride in oil are slowly added to 200 ml of dry tetrahydrofuran, under an atmosphere of nitrogen. The mixture is refluxed then 19 g of ethyl [2-(3-trifluoromethyl-phenyl)-quinoline]-4-carboxylate are introduced. Then a solution of 14.7 g of ethyl [3-(N-benzoyl)piperidyl]acetate in 100 ml of dry tetrahydrofuran is slowly added, in an hour. The mixture is stirred for 2 hours under reflux. Then 20 ml of ethanol followed by 20 ml of water are added, the solvent is removed by distillation under reduced pressure, the residue is taken up with 300 ml of a 5 N aqueous solution of hydrochloric acid and heated under reflux for 13 hours. The aqueous phase is extracted 2 times, each by 200 ml of diethyl ether, filtered, made alkaline by addition of concentrated ammonia and extracted 2 times, each by 200 ml of ethyl acetate. The ethyl acetate phase is dried over magnesium sulfate, treated with 1 g of animal black, filtered, and evaporated under reduced pressure. 5 g of 1-{4-[2-(3-trifluoromethyl-phenyl)]quinolyl}-2-(3-piperidyl)-ethanone are thus obtained. N.M.R. spectrum of the product obtained:

| protons of aromatic nucleus: | $\delta = 7.3$–$8.4$ ppm |
|---|---|
| —N—CH$_2$— and —CO—CH$_2$—: | $\delta = 3$–$4$ ppm |

EXAMPLE 10

1-{4-[2-(4-chloro-phenyl)]quinolyl}-2-(3-piperidyl)-ethanone

The operation is as in Example 3, but starting from 13 g of ethyl [2-(4-chloro-phenyl)-quinoline]-4-carboxylate, 23 ml of a 20% suspension of potassium hydride in oil and 10.9 g of ethyl [3-(N-benzoyl)piperidyl]acetate. 6.8 g of crude product are obtained, which is fixed on a column containing 340 g of silica. After elution with a 9/1 chloroform-diethylamine mixture, 3.5 g of 1-{4-[2-(4-chloro-phenyl)]quinolyl}-2-(3-piperidyl)-ethanone are isolated in the form of an oil. N.M.R. spectrum of the product obtained:

| protons of aromatic nucleus: | $\delta = 7.3$ to $8.4$ ppm |
|---|---|
| —N—CH$_2$— and —CO—CH$_2$—: | $\delta = 3$ to $4$ ppm |

EXAMPLE 11

6-methoxy-4-[3-(3-piperidyl)-propyl]-quinoline

A mixture of 8.2 g of 1-[4-(6-methoxy)quinolyl]-3-(3-piperidyl)-1-propanone, 3.5 ml of 85% hydrazine hydrate and 5.5 g of potassium hydroxide pellets in 30 ml of ethyleneglycol is heated at 180° C. for 45 minutes. After cooling, the reaction mixture is diluted with water, then extracted with chloroform. The organic phase is washed with water, dried over magnesium sulfate and evaporated under reduced pressure. The residue obtained (8.10 g) is absorbed on a column of 400 g of silica. After elution with a 93/7 chloroform-diethylamine mixture, 5.1 g are obtained of 6-methoxy-4-[3-(3-piperidyl)-propyl]-quinoline which, after recrystallization in diethyl ether, melts at 110° C.

EXAMPLE 12

6-methoxy-4-[2-(3-piperidyl)-ethyl]-quinoline

A mixture of 7 g of 1-[4-(6-methoxy)quinolyl]-2-(3-piperidyl)-ethanone and 7 ml of 85% hydrazine hydrate in 100 ml of ethyleneglycol is heated at 180° C. for 15 minutes. It is then cooled to 60° C., then 10 g of potassium hydroxide pellets are added and the mixture is heated at 180° C. for 2 hours. The reaction mixture is diluted with water, and extracted with chloroform. The organic phase is dried over magnesium sulfate and evaporated under reduced pressure. 4.9 g of crude product are thus obtained which is absorbed on a column of 245 g of silica. After elution with a 93/7 chloroform-diethylamine mixture, 2.9 g of 6-methoxy 4-[2-(3-piperidyl)-ethyl]-quinoline are obtained, which are converted into the monohydrochloride. This monohydrochloride melts at 224° C.

EXAMPLE 13

2-phenyl-4-[2-(3-piperidyl)-ethyl]-quinoline

A mixture of 11 g of 1-[4-(2-phenyl)quinolyl]-2-(3-piperidyl)-ethanone and 4.5 ml of 85% hydrazine hydrate in 50 ml of diethyleneglycol is heated at 180° C. for 15 minutes. After cooling to 50° C., 6.7 g of potassium hydroxide pellets are added and the mixture is heated at 180° C. for 3 hours. The reaction mixture is diluted with water, and extracted with ethyl acetate. The organic phase is dried over magnesium sulfate, decolorized with animal black, filtered and evaporated under reduced pressure. 10.2 g of 2-phenyl-4-[2-(3-piperidyl)-ethyl]-quinoline are thus obtained. This last compound is dissolved in acetone and converted by addition of hydrochloric acid into its monohydrochloride, which melts at 206° C.

EXAMPLE 14

2-phenyl-4-[3-(3-piperidyl)-propyl]-quinoline

The operation is as in Example 13, starting from 11.1 g of 1-[4-(2-phenyl)quinolyl]-3-(3-piperidyl)-1-propanone, 11 ml of 85% hydrazine hydrate and 16.6 g of potassium hydroxide. 10.1 g of crude product are obtained, which are absorbed on a column of 610 g of silica. After elution with a 90/10 chloroform-diethylamine mixture, 7.6 g of 2-phenyl-4-[3-(3-piperidyl)-propyl]-quinoline are isolated, which are converted into its monohydrochloride. This monohydrochloride melts at 154° C.

EXAMPLE 15

4-[3-(3-piperidyl)-propyl]-quinoline

The operation is as in Example 13, but starting from 4.3 g of 1-(4-quinolyl)-3-(3-piperidyl)-1-propanone, 1.8 ml of 85% hydrazine hydrate and 2.8 g of potassium hydroxide pellets. 3.4 g of crude product are obtained, from which, after absorption on a column of 340 g of silica and elution with a 9/1 chloroform-diethylamine mixture, 1.4 g of 4-[3-(3-piperidyl)-propyl]-quinoline are isolated. This compound is dissolved in acetone and converted, by addition of hydrochloric acid, into its monohydrochloride, which melts at 161° C.

EXAMPLE 16

2-[3-(3-piperidyl)-propyl]-quinoline

The operation is as in Example 13, but starting from 6 g of 1-(2-quinolyl)-3-(3-piperidyl)-1-propanone, 6 ml of 85% hydrazine hydrate and 5 g of potassium hydroxide pellets. 4.9 g of crude product are obtained. This product is absorbed on a column of 150 g of silica and eluted with a 9/1 chloroform-diethylamine mixture. 1.5 g of 2-[3-(3-piperidyl)-propyl]-quinoline are thus obtained, which melts at 194° C.

EXAMPLE 17

3-[3-(3-piperidyl)-propyl]-quinoline

A mixture of 3 g of 1-(3-quinolyl)-3-(3-piperidyl)-1-propanone, 3 ml of 85% hydrazine hydrate and 3 g of potassium hydroxide pellets in 30 ml of diethyleneglycol is heated at 180° C. for 2 hours 30 minutes. After cooling, the reaction mixture is diluted with water, then extracted with chloroform. The organic phase is washed with water, dried over magnesium sulfate and evaporated under reduced pressure. 2.6 g of crude product are thus obtained, which is fixed on a column of 130 g of silica. After elution with a 9/1 chloroform-diethylamine mixture, 0.85 g of 3-[3-(3-piperidyl)-propyl]-quinoline are isolated, of which the monohydrochloride melts at 180° C.

EXAMPLE 18

6-chloro-2-phenyl-4-[2-(3-piperidyl)-ethyl]-quinoline

A mixture of 4 g of 1-[4-(6-chloro-2-phenyl)quinolyl]-2-(3-piperidyl)-ethanone and 1.9 ml of 85% hydrazine hydrate in 20 ml of diethyleneglycol is heated at 180° C. for 15 minutes. It is cooled to 60° C., then 2.4 g of potassium hydroxide pellets are added, and the mixture is heated at 120° C. for 3 hours 30 minutes. Then the mixture is cooled to 50° C., run into 200 ml of a mixture of water and ice and extracted two times, each by 100 ml of ethyl acetate. The organic phase is washed with water, dried over magnesium sulfate and evaporated under reduced pressure. 3.4 g of 6-chloro-2-phenyl-4-[2-(3-piperidyl)-ethyl]-quinoline are thus obtained. This compound is dissolved in acetone and converted by addition of hydrochloric acid into its monohydrochloride. This latter compound, after recrystallization from methanol containing 2% of water, has a melting point above 260° C.

EXAMPLE 19

4-[2-(3-piperidyl)-ethyl]-2-(3-trifluoromethyl-phenyl)-quinoline

A mixture of 4.5 g of 1-{4-[2-(3-trifluoromethyl-phenyl)]-quinolyl}-2-(3-piperidyl)-ethanone and 1.8 ml of 85% hydrazine hydrate in 40 ml of diethyleneglycol is heated at 160° C. for 30 minutes. It is cooled to 100° C., then 1.8 g of potassium hydroxide pellets are added and the mixture is heated at 180° C. for 4 hours. The reaction mixture is then diluted with water, and extracted with diethyl ether. The organic phase is dried over magnesium sulfate and evaporated under reduced pressure. The residue obtained is fixed on a column of silica and eluted with a 9/1 chloroform-diethylamine mixture, 2.2 g of 4-[2-(3-piperidyl)ethyl]-2-(3-trifluoromethyl-phenyl)-quinoline are thus isolated. This compound is dissolved in acetone and converted by addition of hydrochloric acid into its monohydrochloride, which melts at 228° C.

EXAMPLE 20

2-(4-chloro-phenyl)-4-[2-(3-piperidyl)-ethyl]-quinoline

A mixture of 3.3 g of 1-{4-[2-(4-chloro-phenyl)-]quinolyl}-2-(3-piperidyl)-ethanone and 1.5 ml of 85% hydrazine hydrate in 35 ml of diethyleneglycol is heated at 160° C. for 1 hour. Then there is added to the reaction medium 1 ml of 85% hydrazine hydrate and the mixture is heated at 175° C. for 1 hour. The mixture is cooled to 100° C., then 1.5 g of potassium hydroxide pellets is added and the mixture is heated at 175° C. for 2 hours. The reaction mixture is diluted with water, extracted with chloroform, and the organic phase is dried over magnesium sulfate and evaporated under reduced pressure. 3 g are thus obtained of 2-(4-chloro-phenyl)-4-[2-(3-piperidyl)-ethyl]-quinoline. This last compound is dissolved in acetone and converted by addition of hydrochloric acid into its monohydrochloride, which melts at 155° C.

EXAMPLE 21

4-[2-(2-piperidyl)-ethyl]-quinoline (1) Preparation of the 2-(2-pyridyl)-1-(4-quinolyl)-ethanone.

4.05 g of diisopropylamine are added to 30 ml of dry tetrahydrofuran and placed under an atmosphere of nitrogen. The solution is stirred, then cooled to −70° C. Then 18.8 ml of a 1.6 molar solution of butyllithium in hexane are introduced in 5 minutes, then after stabilization of the temperature at −70° C., 2.8 g of 2-methyl-pyridine are introduced in 5 minutes. The temperature is again stabilized at −70° C., and then 2 g of ethyl quinoline-4-carboxylate are introduced in three minutes. At the end of the introduction, 20 ml of ethanol are added to the reaction medium. The temperature is allowed to rise to −20° C., then 20 ml of water are added. By evaporation under reduced pressure of the reaction medium, 2 g of residue are isolated, which is fixed on a column of 100 g of silica. After elution with ethyl acetate, 1.5 g of 2-(2-pyridyl)-1-(4-quinolyl)-ethanone are isolated.

(2) Preparation of the 4-[2-(2-pyridyl)-ethyl]-quinoline.

A mixture of 15.8 g of 2-(2-pyridyl)-1-(4-quinolyl)-ethanone and 25 ml of 85% hydrazine hydrate in 250 ml of diethylene-glycol is heated at 160° C. for 30 minutes. After cooling to 60° C., 22 g of sodium hydroxide pellets are added and the mixture is heated at 160° C. for 2 hours. The reaction mixture is diluted with water, then extracted 3 times, each by 300 ml of methylene chloride. The organic phase is dried over magnesium sulfate and evaporated under reduced pressure. 12.5 g are thus obtained of 4-[-2-(2-pyridyl)-ethyl]-quinoline in the form of a lacquer. N.M.R. spectrum of the product obtained:

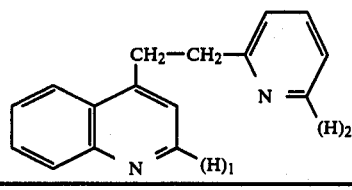

| | |
|---|---|
| (H)₁: | δ = 8.7 ppm |
| (H)₂: | δ = 8.5 ppm |
| CH₂—Ar: | δ = 3 to 3.6 ppm |

(3) Preparation of the 4[2-(2-piperidyl)-ethyl]-quinoline.

30 ml of a 10 N aqueous solution of acetic acid are added to a solution containing 7 g of 4-[2-(2-pyridyl)-ethyl]-quinoline in 700 ml of ethanol, then 1.4 g of 82% platinum oxide is added as catalyst. Hydrogenation is effected at 45° C. under a hydrogen pressure equal to the normal pressure (1 bar) for 24 hours, being careful to replace the catalyst used every eight hours by fresh catalyst. At the end of the 24 hours (the quantity of hydrogen absorbed is then 2.9 liters), the catalyst is removed by filtration, the ethanol is evaporated under reduced pressure and the residue is taken up with 200 ml of water. The aqueous phase is extracted with chloroform, then made alkaline with concentrated ammonia and extracted with methylene chloride. The methylene chloride phase is dried over magnesium sulfate and evaporated under reduced pressure. The oily residue (6.3 g) is fixed on a column containing 630 g of silica, then eluted with a 9/1 toluene-diethylamine mixture. 1.9 g are thus isolated of 4-[2-(2-piperidyl)-ethyl]-quinoline.

After recrystallization in isopropyl ether, this product melts at 83° C.

EXAMPLE 22

2-phenyl-4-[2-(2-piperidyl)-ethyl]-quinoline (1) Preparation of the 2-(2-pyridyl)-1-[4-(2-phenyl)-quinolyl]-ethanone.

40.5 g of diisopropylamine are added to 200 ml of dry tetrahydrofuran, placed under an atmosphere of nitrogen. The solution is stirred, then cooled to −60° C. 200 ml of a 15% solution of butyllithium in hexane are then introduced in 10 minutes. When the temperature has been stabilized at −60° C., a solution of 28 g of 2-methyl-pyridine in 100 ml of dry tetrahydrofuran is introduced in 10 minutes. The mixture is cooled to −60° C., then a solution of 27.7 g of ethyl 2-phenyl-quinoline)-4-carboxylate in 100 ml of dry tetrahydrofuran is introduced in 10 minutes. The reaction medium is stirred for 20 minutes at −60° C., then 100 ml of ethanol are introduced drop by drop. The temperature is brought back to −20° C., then 100 ml of water are introduced drop by drop, and the mixture is stirred for a further two hours. The precipitate obtained is filtered, washed 3 times, each by 300 ml of water, then 3 times, each by 100 ml of acetone and finally with 100 ml of diethyl ether. 22 g are thus obtained of 1-[4-(2-phenyl)quinolyl]-2-(2-pyridyl)-ethanone, which melts at about 250° C.

(2) Preparation of the 2-phenyl 4-[2-(2-pyridyl)-ethyl]-quinoline.

A mixture of 13 g of 1-[4-(2-phenyl)quinolyl]-2-(2-pyridyl)-ethanone and 2.3 ml of 85% hydrazine hydrate in 40 ml of diethyleneglycol is heated at 180° C. for 1 hour and 15 minutes. It is cooled to the ambient temperature, then 2 g of sodium hydroxide pellets are added and the mixture is heated at 180° C. for 5 hours. The reaction mixture is diluted with water then extracted with chloroform. The organic phase is dried over magnesium sulfate and evaporated under reduced pressure. 5 g of an oily residue are thus obtained, which is fixed on a column containing 500 g of silica and is eluted with a 5/4/1 chloroform/cyclohexane/diethylamine mixture under a pressure of 5 bars. 3 g are thus isolated of 2-phenyl-4-[2-(2-pyridyl)-ethyl]-quinoline in the form of an oil. N.M.R. Spectrum of the product obtained:

| protons of the aromatic nucleus: | $\delta = 7$ to 8.2 ppm |
|---|---|
| CH$_2$—Ar | $\delta = 3$ to 3.6 ppm |

(3) Preparation of 2-phenyl-4-[2-(2-piperidyl)-ethyl]-quinoline 4.55 ml of concentrated acetic acid are added to a solution containing 2.5 g of 2-phenyl-4-[2-(2-pyridyl)-ethyl]-quinoline in 250 ml of ethanol, then 0.5 g of 82% platinum oxide is added as catalyst. Hydrogenation is effected at 30° C., under a hydrogen pressure equal to the normal pressure for 6 hours, at the end of which time 700 ml of hydrogen have been absorbed. The catalyst is eliminated by filtration. The ethanol is evaporated under reduced pressure and the residue is taken up with 200 ml of water. The aqueous phase is made alkaline by means of concentrated ammonia, and extracted with methylene chloride. The organic phase is dried over magnesium sulfate and evaporated under reduced pressure. The residue obtained is fixed on a column of 200 g of silica and eluted with a 9/1 toluene-diethylamine mixture. 0.65 g are thus isolated of 2-phenyl-4-[2-(2-piperidyl)-ethyl]-quinoline in the form of an oil. This compound is dissolved in acetone and converted, by addition of hydrochloric acid, to its dihydrochloride, which melts at 200° C.

EXAMPLE 23

4-{2-[3-(1-methyl)piperidyl]-ethyl}-2-phenyl-quinoline

A mixture containing 2.8 g of 2-phenyl-4-[2-(3-piperidyl)ethyl]-quinoline, 20 ml of formic acid and 20 ml of 37% aqueous solution of formaldehyde is heated at 95°-100° C. for 2 hours and 30 minutes. After cooling to the ambient temperature, the reaction medium is run into a liter of water, then extracted with a liter of ethyl acetate. The organic phase is dried over magnesium sulfate and evaporated under reduced pressure. The residue is fixed on a column of 500 g of silica and eluted with a 95/5 chloroform-diethylamine mixture, under a pressure of 5 bars. 1.6 g are thus obtained of 4-{2-[3-(1-methyl)-piperidyl]-ethyl}-2-phenyl-quinoline. This compound is dissolved in acetone and converted, by addition of hydrochloric acid, into its monohydrochloride, which melts at 177° C.

EXAMPLE 24

4-{3-[3-(1-methyl)piperidyl]-propyl}-2-phenyl-quinoline

The operation is as in Example 23, but starting from 3.8 g of 2-phenyl-4-[3-(3-piperidyl)-propyl]-quinoline, 35 ml of formic acid and 35 ml of 37% aqueous solution of formaldehyde. The crude product (3 g) obtained after extraction with ethyl acetate and evaporation of the solvent is fixed on a column containing 400 g of silica and eluted with a 90/10 chloroform-diethylamine mixture. 1.6 g are thus obtained of 4-{3-[3-(1-methyl)-piperidyl]-propyl}-2-phenyl-quinoline, of which the monohydrochloride melts at 163° C.

EXAMPLE 25

4-{2-[3-(1-benzyl)piperidyl]-ethyl}-2-phenyl-quinoline (1) Preparation of the 4-{2-[3-(1-benzoyl-piperidyl]-ethyl}-2-phenyl-quinoline.

2.77 ml of triethylamine are added to a stirred suspension of 3.52 g of 2-phenyl-4-[2-(3-piperidyl)-ethyl]-quinoline hydrochloride in 30 ml of chloroform. The mixture is cooled to +3° C. and 1.5 ml of benzoyl chloride in 20 ml of chloroform is introduced, then the mixture is left with stirring for an hour at the ambient temperature. Then 50 ml of water are added with good stirring. The organic phase is separated by decantation, washed successively two times by 30 ml of water, 50 ml of a 0.1 N solution of acetic acid and 50 ml of water, then dried over magnesium sulfate. After evaporation of the solvent under reduced pressure, 4.2 g are obtained of 4-{2-[3-(1-benzoyl)piperidyl]-ethyl}-2-phenyl-quinoline in the form of an oil.

(2) Preparation of the 4-{2-[3-(1-benzyl)piperidyl]-ethyl}-2-phenyl-quinoline.

380 mg of aluminum lithium hydride are slowly added, portionwise, to 30 ml of dry tetrahydrofuran. The stirred suspension is cooled to +3° C. and there is added in 30 minutes a solution of 4.5 g of 4-{2-[3-(1-benzoyl)piperidyl]-ethyl}-2-phenyl-quinoline in 30 ml of tetrahydrofuran. The mixture is stirred for an hour at the ambient temperature, then heated under reflux for two hours. It is cooled to the ambient temperature. A further 500 mg of aluminum lithium hydride is added portionwise and the mixture is heated under reflux for two hours. The mixture is cooled to the ambient temperature, then there are introduced very slowly and successively 1.17 ml of water, 0.43 ml of a 10 N aqueous solution of sodium hydroxide, then 3.90 ml of water. The insoluble mineral products formed are separated by filtration and washed with 30 ml of tetrahydrofuran. The filtrate and the washings are collected, dried over magnesium sulfate and evaporated. The residue obtained is fixed on a column of 200 g of silica and eluted with a 95/5 toluene-diethylamine mixture. 1 g is thus isolated of 4-{2-[3-(1-benzyl)piperidyl]-ethyl}-2-phenyl-quinoline, of which the monohydrochloride melts at 178° C.

EXAMPLE 26

4-[2-{3-[1-(2-phenyl-ethyl)]piperidyl}-ethyl]-2-phenyl-quinoline (1) Preparation of the 2-phenyl-4-{2-[3-(1-phenylacetyl)piperidyl]-ethyl}-quinoline.

2.77 ml of triethylamine are added to a stirred suspension of 3.52 g of 2-phenyl-4-[2-(3-piperidyl)-ethyl]-quinoline hydrochloride in 30 ml of chloroform. The mixture is cooled to +3° C. and a solution of 2 g of phenylacetyl chloride in 10 ml of chloroform is added drop by drop. The mixture is stirred for two hours at the ambient temperature. Then 20 ml of water are added with good stirring. The organic phase is separated by decantation, washed with water, dried over anhydrous sodium sulfate and evaporated under reduced pressure. 4.2 g are thus obtained of 4-{2-[3-(1-phenylacetyl)-piperidyl]-ethyl}-2-phenyl-quinoline in the form of an oil.

(2) Preparation of the 4-[2-{3-[1-(2-phenyl-ethyl)-]piperidyl}-ethyl]-2-phenyl-quinoline.

380 mg of aluminum lithium hydride are slow added, portionwise, to 30 ml of dry tetrahydrofuran. The stirred suspension is cooled to +3° C. and there is added in a period of 30 minutes a solution of 4.2 g of 2-phenyl-4-{2-[3-(1-phenylacetyl)piperidyl]-ethyl}-quinoline in 30 ml of tetrahydrofuran. The mixture is stirred for 3 hours at the ambient temperature. Then 0.65 ml of water, 0.21 ml of a 10 N aqueous solution of sodium hydroxide and 1.9 ml of water are successively and very slowly introduced. The insoluble mineral products formed are separated by filtration and washed with 30 ml of tetrahydrofuran. The filtrate and the washings are collected, dried over magnesium sulfate and evaporated. The residue obtained is fixed on a column of 400 g of silica and eluted with a 95/5 chloroform-diethylamine mixture. 2.3 g are thus isolated of 4-[2-{3-[1-(2-phenyl-ethyl]piperidyl}-ethyl]-2-phenyl-quinoline. This compound is dissolved in acetone and converted, by addition of hydrochloric acid, into its monohydrochloride, which melts at 204° C.

EXAMPLE 27

4-{2-[3-(1-allyl)piperidyl]-ethyl}-2-phenyl-quinoline 1.9 g of potassium carbonate and 1.18 ml of allyl chloride are added to a solution of 3.15 g of 2-phenyl-4-[2-(3-piperidyl)ethyl]-quinoline in 30 ml of tetrahydrofuran, placed under an atmosphere of nitrogen. The mixture is stirred for 48 hours at the ambient temperature, then 2 ml of water are added and the mixture is left for an hour with good stirring. After evaporation under reduced pressure, a residue is isolated which is taken up with 100 ml of water and 50 ml of ethyl acetate. The organic phase is separated, washed with water, dried over magnesium sulfate and evaporated under reduced pressure. The residue obtained is fixed on a column containing 130 g of silica and eluted with a 98/2 toluene-diethylamine mixture. 1 g is thus isolated of 4-{2-[3-(1-allyl)piperidyl]-ethyl}-2-phenyl-quinoline, which melts at 202° C.

EXAMPLE 28

1-[4-(2-phenyl)quinolyl]-2-(3-pyrrolidinyl)-1-ethanone (1) Preparation of the methyl [3-(N-benzoyl)pyrrolidinyl]acetate.

104 g of anhydrous potassium carbonate are added to a stirred solution of 38.1 g of methyl (3-pyrrolidinyl)acetate in 800 ml of chloroform. Stirring is continued for an hour at the ambient temperature, then the mixture is cooled to 10° C. and 36 ml of benzoyl chloride are slowly introduced in a period of 30 minutes. The mixture is stirred for 12 hours. The mineral salts are removed by filtration and washed with chloroform. The chloroformic phases are collected, washed successively with 250 ml of water, 250 ml of a normal aqueous solution of hydrochloric acid, 200 ml of a 5% aqueous solution of sodium bicarbonate and finally 250 ml of water, dried over magnesium sulfate and evaporated under reduced pressure. The residue obtained if fixed on a column containing 800 g of silica and eluted with ethyl acetate. 14.3 g are thus isolated of methyl [3-(N-benzoyl)pyrrolidinyl]acetate. N.M.R. Spectrum of the product obtained:

| protons of the aromatic nucleus: | $\delta = 7.4$ ppm |
| --- | --- |
| —CH$_2$—CO: | $\delta = 2.4$ ppm |
| —CH$_2$—N—CO: | $\delta = 3$ to 4 ppm |

The methyl (3-pyrrolidinyl)acetate can be prepared by the process described in Japanese Pat. No. 4820/59.

(2) Preparation of the 1-[4-(2-phenyl)quinolyl]-2-(3-pyrrolidinyl)-1-ethanone.

48 ml of a 20% suspension of potassium hydride in oil are slowly added to 140 ml of dry tetrahydrofuran, placed under an atmosphere of nitrogen. Then 11.6 g of ethyl (2-phenyl-quinoline)-4-carboxylate are introduced and subsequently a solution of 8.6 g of methyl [3-(N-benzoyl)pyrrolidinyl]acetate in 70 ml of dry tetrahydrofuran is slowly added, in a period of 2 hours. The mixture is stirred for 1 hour and 30 minutes at the ambient temperature, and then 35 ml of absolute ethanol are added. The solvent is eliminated by distillation under reduced pressure. The residue is taken up with 175 ml of a 5 N aqueous solution of hydrochloric acid and heated under reflux for 13 hours. The aqueous phase is extracted two times, each by 200 ml of diethyl ether, then is evaporated to dryness. The residue obtained is washed several times with acetone. 13.3 g are thus obtained of 1-[4-(2-phenyl)quinolyl]-2-(3-pyrrolidinyl)-1-ethanone in the form of the dihydrochloride. N.M.R. Spectrum of the product obtained:

| protons of the aromatic nucleus: | $\delta = 7.3$ to 8.4 ppm |
| --- | --- |
| —CH$_2$—CO and CH$_2$—N—: | $\delta = 2.5$ to 3.2 ppm |

EXAMPLE 29

2-phenyl-4-[2-(3-pyrrolidinyl)-ethyl]-quinoline

A mixture of 13.3 g of 1-[4-(2-phenyl)quinolyl]-2-(3-pyrrolidinyl)-1-ethanone dihydrochloride and 8.3 g of 85% hydrazine hydrate in 40 ml of diethyleneglycol is heated at 160° C. for 15 minutes. The mixture is cooled to 100° C., then 9.8 g of potassium hydroxide pellets are added portionwise, and heating at 160° C. is effected for 5 hours. The reaction mixture is diluted with water, extracted 3 times, each by 100 ml of methylene chloride, and the organic phase is dried over magnesium sulfate and evaporated under reduced pressure. The residue obtained is absorbed on a column of 250 g of silica and eluted with a 90/10 chloroformdiethylamine mixture. 5.5 g are thus isolated of 2-phenyl-4-[2-(3-pyrrolidinyl)-ethyl]-quinoline in the form of an oil. This compound is dissolved in isopropanol and converted, by addition of hydrochloric acid, into its monohydrochloride, which melts at 140° C.

EXAMPLE 30

4-[3-(2-piperidyl)-propyl]-2-phenyl-quinoline.

(1) Preparation of ethyl [2-(1-triphenylmethyl)piperidine]acetate 31 ml of triethylamine are added to a stirred solution of 33.8 g of ethyl (2-piperidine)acetate in 700 ml of chloroform. The solution is cooled to 0° C., then 72.6 g of triphenylmethyl chloride areslowly added, portionwise. The temperature is allowed to rise to 20° C. and the mixture is left for 18 hours with stirring. Then 18.2 g of triphenylmethyl chloride and 8 ml of triethylamine are added. The mixture is stirred for 3 hours, then a further 9 g of triphenylmethyl chloride and 4 ml of triethylamine is added. The reaction mixture is evaporated under reduced pressure and the residue is taken up with 600 ml of diethyl ether. The precipitate of triethylamine hydrochloride formed is filtered and the filtrate is evaporated. An oily yellow residue is thus obtained which is taken up with petroleum ether, and the crystals obtained are filtered off. Ethyl [2-(1-triphenylmethyl)-piperidine]acetate is thus obtained, which melts at 95° C.

(2) Preparation of the [2-(1-triphenylmethyl)-piperidine]-ethanol.

15.2 g of aluminum lithium hydride are slowly added, portionwise, to 600 ml of anhydrous tetrahydrofuran, placed under an atmosphere of nitrogen. The stirred suspension is cooled to 0° C. and 82 g of ethyl [2-(1-triphenylmethyl)piperidine]acetate are slowly added in a period of an hour. The temperature is allowed to return to the ambient temperature and the reaction medium is stirred for two hours. It is then cooled to 0° C. and 17 ml of water, 12.6 ml of a 5 N aqueous solution of sodium hydroxide and 59 ml of water are successively added. The mineral products are separated by filtration and washed with boiling methylene chloride. The filtrate and the washings are collected, dried over magnesium sulfate and evaporated. 127.5 g of an oily residue are thus obtained. This residue is fixed on a column of 1200 g of silica and eluted with an 80/20 cyclohexane-ethyl acetate mixture. 36.5 g of [2-(1-triphenylmethyl)-piperidine]-ethanol are thus isolated, which melts at 165° C.

(3) Preparation of the 2-[2-(p-tolylsulfonyloxy)-ethyl]-1-triphenylmethyl-piperidine.

15 g of p-methylphenylsulfonyl chloride are added all at once to a solution of 15 g of [2-(1-triphenylmethyl)-piperidine]ethanol in 150 ml of pyridine and cooled to 0° C. The mixture is stirred for two hours at 0° C., then the reaction mixture is run slowly, with stirring, into 1500 ml of water. The precipitate obtained is filtered off, washed with water, dried, and there are thus obtained 17.9 g of 2-[2-(p-tolylsulfonyloxy)-ethyl]-1-triphenylmethyl-piperidine. N.M.R. Spectrum of the product obtained:

| protons of the aromatic nuclei: | $\delta = 7$ to 7.6 ppm |
| —CH$_2$—O: | $\delta = 3.6$ ppm |
| —CH$_2$—N—: | $\delta = 2.8$ to 3.2 ppm |

(4) Preparation of the 4-[3-(2-piperidyl)-propyl]-2-phenylquinoline.

5.4 ml of diisopropylamine are added to 40 ml of dry tetrahydrofuran, placed under an atmosphere of nitrogen. The solution is stirred, cooled to −60° C. and there are introduced, in a period of 15 minutes, 15 ml of a 2 M solution of butyllithium in hexane. After stabilization of the temperature at −60° C., a solution is introduced of 6.6 g of 2-phenyl-4-methyl-quinoline in 20 ml of dry tetrahydrofuran. The mixture is stirred for 20 minutes at −60° C., then a solution of 10.5 g of 2-[2-(p-tolylsulfonyloxy)-ethyl]-1-triphenylmethyl-piperidine in 50 ml of dry tetrahydrofuran is slowly introduced. The mixture is reheated to the ambient temperature and is left for 3 hours and 30 minutes with stirring. Then 50 ml of water are added, the mixture is evaporated under reduced pressure and the residue is taken up with 200 ml of diethyl ether and 50 ml of water. The ethereal phase is decanted, washed with water, dried over magnesium sulfate and concentrated.

The residue obtained is taken up with 200 ml of an N aqueous solution of hydrochloric acid, and stirred for 10 minutes at the ambient temperature. Then the aqueous phase is washed two times, each by 200 ml of diethyl ether, brought to pH 10 by addition of a concentrated solution of sodium hydroxide and extracted with ethyl acetate. The ethyl acetate extract is evaporated under reduced pressure.

The residue obtained is fixed on a column containing 400 g of silica and eluted with a 70/20/10 cyclohexane/chloroform/diethylamine mixture. 2.1 g are thus isolated of 4-[3-(2-piperidyl)-propyl]-2-phenyl-quinoline in the form of an oil. The monohydrochloride of this compound melts at 184° C.

EXAMPLE 31

1-[4-(2-phenyl)quinolyl]-2-(3-piperidyl)-ethanol 0.6 g of sodium borohydride is added, portionwise, to a solution, stirred and cooled to +10° C., of 3 g of racemic 1-[4-(2-phenyl)quinolyl]-2-(3-piperidyl)-ethanone hydrochloride, obtained as indicated in Example 3, in 50 ml of methanol. The mixture is stirred for one hour at the ambient temperature, then 50 ml of water and 50 ml of ethyl acetate are slowly introduced. The organic phase is separated by decantation. The aqueous phase is extracted two times, each by 100 ml of ethyl acetate. The organic phases are collected, washed with 30 ml of water, dried over magnesium sulfate and evaporated under reduced pressure. 2.8 g are thus obtained of 1-[4-(2-phenyl)quinolyl]-2-(3-piperidyl)ethanol in the form of a mixture of the two racemic diastereoisomers (the analysis of the mixture by liquid chromatography shows that the percentage of each racemic diastereoisomer is about 50%). The dihydrochloride of the product obtained melts at 230° C. (with decomposition).

Pharmacological Properties

1. Affinity for the Cerebral Binding Sites of the Benzodiazepines

This affinity is measured by the capacity of the products for displacing the tritiated Diazepam ($^3$H Diazepam) from its binding site and is expressed by a value $K_i$, in micromoles, which is calculated by the formula:

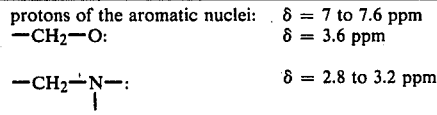

in which C represents the concentration of $^3$H Diazepam, $K_D$ is a constant of affinity equal to 2.74 μM and IC$_{50}$ is the concentration necessary to obtain an inhibition of 50% of the binding of the $^3$H Diazepam.

The products have been tested by using the method of Mohler and Coll., Life Sciences, 20, 2101 (1977) and the results obtained are collected in the following Table 1:

TABLE 1

| Products | $K_i$ (μM) |
|---|---|
| Example 1 | 2 |

TABLE 1-continued

| Products | $K_i$ ($\mu$M) |
| --- | --- |
| Example 4 | 0.8 |
| Example 11 | 5.5 |
| Example 13 | 0.1 |
| Example 14 | 1 |
| Example 20 | 1.6 |
| Example 22 | 0.6 |
| Example 23 | 0.9 |
| Example 24 | 3 |
| Example 29 | 0.7 |
| Example 30 | 2.7 |

2. Antiarrhythmic Activity

The antiarrhythmic activity of the compounds of the present invention has been demonstrated by means of the aconitine test on the rat.

The principle of the method rests on the time of induction of the ventricular arrhythmias caused by the aconitine which is slowly perfused in rats. An antiarrhythmic substance retards the appearance of the arrhythmias and the delay is proportional to the activity of the molecule.

Groups of 5 male rats are used. An individual annesthesia is realized (10% urethane: 1 g/kg/ip) in order to permit a catheterization of the vein of the penis. The electrocardiogram is recorded. At time T=O the substance studied is injected in the form of an aqueous solution, at the rate of 2.5 ml of solution per kg in 30 seconds. At time T=90 seconds, say 1 minute after the end of the injection, the aconitine is perfused at the rate of 20 µg per minute, until the appearance of extra supraventricular systoles. The time of perfusion of the aconitine is noted.

The results are expressed by $ED_{50}$, which is the dose of product in mg/kg which increases by 50% the time of perfusion of the aconitine in comparison with the perfusion time of aconitine for the control animals.

The results obtained are collected in the following Table 2.

TABLE 2

| Products | $ED_{50}$ mg/kg (i.v.) |
| --- | --- |
| Example 3 | 2.8 |
| Example 11 | 7.8 |
| Example 14 | 2.2 |

Toxicological Properties

The acute toxicities of the compounds according to the invention have been determined on the male mouse $CD_1$ (Charles River) administered orally. The $LD_{50}$ have been calculated, after 3 days observation, by the cumulative method of J. J. Reed and H. Muench. (Amer. J. Hyg. 1938, 27, 493).

The compounds according to the invention behave as substances of relatively little toxicity to mice, since the $LD_{50}$ of the compounds are between 200 and 1000 mg/kg.

Therapeutic Utilization

The compounds of the invention and their pharmaceutically acceptable salts may be used in human therapeutics, in the form of compressed tablets, capsules, gelatin-coated pills, suppositories, ingestable or injectable solutions, etc., as antiarrhythmics, hypnotics, anticonvulsivants and for the treatment of states of anxiety and various psychoneurotic states.

The posology depends on the effects required and on the method of administration used. For example, taken orally, it can be between 5 and 250 mg of active substance per day, with unitary doses ranging from 1 to 50 mg.

What is claimed is:

1. Compounds of the formula:

$$\text{(I)}$$

in which R is fixed in position 2 or 4 on the cycle of the quinoline and represents a phenyl, pyridyl or thienyl group, or a phenyl group substituted by one or two substituents selected from the halogen atoms, the alkyl, alkoxy and alkylthio groups having 1 to 4 carbon atoms and the trifluoromethyl group, X is fixed in position 5, 6, 7 or 8 on the cycle of the quinoline and represents a hydrogen or halogen atom, an alkyl, alkoxy or alkylthio group having 1 to 4 carbon atoms or the trifluoromethyl group, $R_1$ represents a hydrogen atom, an alkyl group containing from 1 to 4 carbon atoms, an alkenyl group containing 3 or 4 carbon atoms or an arylalkyl group of which the alkyl part contains 1 to 3 carbon atoms, A represents a CO, CHOH or $CH_2$ group, n is a whole number equal to 1 or 2, p is a whole number equal to 1 or 2, the group:

$$-A-(CH_2)_n-N(R_1)-(CH_2)_p$$

is fixed in position 4 or 2 on the cycle of the quinoline, and the group is fixed in position 2 or 3 on the nitrogen heterocycle:

their diastereoisomers, racemic and enantiomers, and their salts of addition with mineral or organic acids.

2. Compounds according to claim 1 in which X is a hydrogen atom, R is a phenyl group and n is equal to 1.

3. Compound according to claim 2 of the formula:

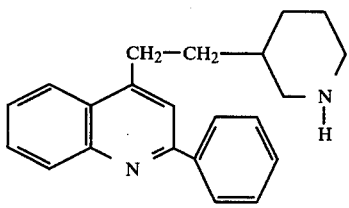

and its salts of addition with the mineral or organic acids.

4. A medicament, useful as an antiarrhythmic, hypnotic, anticonvulsivant and for the treatment of states of anxiety and various psychoneurotic states, which contains a pharmaceutically acceptable carrier and, as the active principle, 1 to 50 mg per unit dose of a compound corresponding to formula (I) of claim 1 or a salt of such a compound with a pharmaceutically acceptable acid.

5. Medicament according to claim 4 which contains as active principle, 1 to 50 mg per unit dose of the compound of the formula:

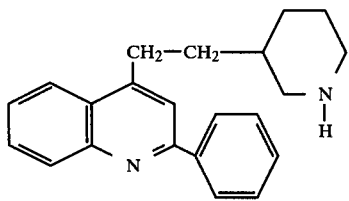

or a salt of this compound with a pharmaceutically acceptable acid.

6. A process for treating a human suffering from anxiety, which comprises orally administering to said human 5 to 250 mg per day of a compound corresponding to formula (I) of claim 1 or a salt thereof with a pharmaceutically acceptable acid.

7. A process according to claim 6, which comprises orally administering 5 to 250 mg per day of the compound:

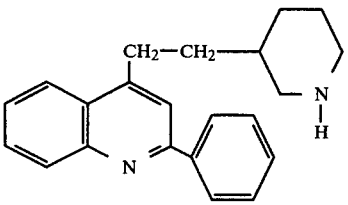

or a salt thereof with a pharmaceutically acceptable acid.

8. The compound according to claim 1 which is 2-phenyl-4-[2-(2-piperidyl)-ethyl]-quinoline.

9. The compound according to claim 1 which is 2-phenyl-4-[2-(3-pyrrolidinyl)-ethyl]-quinoline.

10. The compound according to claim 1 which is 1-[4-(2-phenyl)quinolyl]-2-(3-piperidyl)-ethanone.

11. The compound according to claim 1 which is 1-[4-(2-phenyl)quinolyl]-3-(3-piperidyl)-1-propanone.

12. The compound according to claim 1 which is 2-phenyl-4-[3-(3-piperidyl)-propyl]-quinoline.

13. The compound according to claim 1 which is 4-{2-[3-(1-methyl)piperidyl]-ethyl}-2-phenyl-quinoline.

14. The compound according to claim 1 which is 1-[4-(2-phenyl)quinolyl]-2-(3-pyrrolidinyl)-1-ethanone.

15. A medicament, useful as an antiarrhythmic, hypnotic, anticonvulsivant and for the treatment of states of anxiety and various psychoneurotic states, which contains a pharmaceutically acceptable carrier and, as the active principle, 1 to 50 mg per dose of a compound according to claim 2 or a salt of such a compound with a pharmaceutically acceptable acid.

16. A process for treating a human suffering from anxiety, which comprises orally administering to said human 5 to 250 mg per day of a compound according to claim 2 or a salt thereof with a pharmaceutically acceptable acid.

* * * * *